US012403062B2

(12) United States Patent
Coleman

(10) Patent No.: US 12,403,062 B2
(45) Date of Patent: Sep. 2, 2025

(54) CRUTCH ASSEMBLY CONSTRUCTED USING A PAIR OF HIKING POLES

(71) Applicant: Daniel R Coleman, Yakima, WA (US)

(72) Inventor: Daniel R Coleman, Yakima, WA (US)

( * ) Notice: Subject to any disclaimer, the term of this patent is extended or adjusted under 35 U.S.C. 154(b) by 270 days.

(21) Appl. No.: 18/233,066

(22) Filed: Aug. 11, 2023

(65) Prior Publication Data

US 2025/0050175 A1 Feb. 13, 2025

(51) Int. Cl.
*A61H 3/02* (2006.01)
*A45B 3/00* (2006.01)
*A61F 5/058* (2006.01)
*A63C 11/00* (2006.01)
*A63C 11/22* (2006.01)
*A63H 11/00* (2006.01)

(52) U.S. Cl.
CPC ............... *A61H 3/02* (2013.01); *A45B 3/00* (2013.01); *A61F 5/0585* (2013.01); *A63C 11/002* (2013.01); *A63C 11/22* (2013.01); *A45B 2200/055* (2013.01); *A61H 2003/025* (2013.01)

(58) Field of Classification Search
CPC .. A62H 3/02; A61H 2003/025; A63C 11/002; A63C 11/222; A63C 11/2224; A63C 11/2228; A63C 11/22; A45B 3/00; A45B 2200/055; A61F 5/0585
USPC ............... 135/68, 72, 73, 76; 280/819, 820
See application file for complete search history.

(56) References Cited

U.S. PATENT DOCUMENTS

| | | | | |
|---|---|---|---|---|
| 3,902,731 | A * | 9/1975 | Fagen | A47C 1/14 280/812 |
| 6,257,258 | B1 * | 7/2001 | Smith | A61H 3/02 135/66 |
| 6,397,868 | B1 * | 6/2002 | Smith | A61H 3/02 135/66 |
| 7,007,704 | B2 * | 3/2006 | Luckstead | A45B 7/00 135/65 |
| D780,868 | S * | 3/2017 | Schneck | D21/767 |
| 2004/0090060 | A1 * | 5/2004 | Milan | A63C 11/001 280/820 |
| 2019/0183718 | A1 * | 6/2019 | Scott | A61H 3/02 |

* cited by examiner

*Primary Examiner* — Robert Canfield
(74) *Attorney, Agent, or Firm* — Alloy Patent Law; Walker Griffin Weitzel

(57) ABSTRACT

The present disclosure relates to methods of constructing a crutch as well as a traction splint by utilizing a pair of hiking poles. Embodiments of the present invention further discloses a crutch assembly including a pair of hiking poles arranged and interconnected in a substantially V-shaped formation, a plurality of fasteners, and an attachment. The crutch assembly is configured for partial weight bearing and allows a hiker with a mild injury to travel to a trail or a medical help facility. The traction splint provides the hiker with the ability to move themselves to an assistance point, and eliminates the risk of serious deterioration due to hazardous environmental conditions and prolonged pain, swelling, etc.

11 Claims, 22 Drawing Sheets

CRUTCH ASSEMBLY CONSTRUCTED USING A PAIR OF HIKING POLES

FIELD OF THE INVENTION

The present invention relates to the field of medical assistance devices and methods of constructing medical assistance devices, and more particularly, the present invention relates to methods of constructing crutch as well as traction splint by utilizing a pair of hiking poles.

BACKGROUND

Hiking poles also referred to as trekking poles, hiking sticks, or walking poles are commonly used by hikers to assist with their rhythm, provide stability, and reduce strain on joints on rough terrain. Generally, a hiking pole includes an elongated pole that serves to support the weight of the hiker, a tip to provide contact of the hiking pole with the ground, a handle for providing a gripping surface for the hands of the hiker, and a wrist strap to prevent accidental release of the handle of the hiking pole from hands of the hiker.

Often, many hikers experience a lower extremity injury or pain on the hiking trail, on organs such as the foot, ankle, and knee. The injured hikers require a mobility aid such as but not limited to a crutch to assist them in walking. Generally, hiking trails are located far from medical help facilities and thus, it is not possible to arrange crutch for injured hikers. Further, carrying crutches is not feasible as the hiker has to carry extra weight in the form of a crutch which may not be used at all times. Further, hiking involves traveling on rough and difficult terrains such as mountains, and carrying extra weight in the form of crutches could fatigue the hiker.

Providing medical assistance to injured hikers is a high-priority medical task and if the injured hiker is left untreated, it could lead to serious health hazards such as but not limited to: dehydration, frostbite, sunburn, and so on. Further, the injured hiker can encounter hazardous environmental conditions such as animal attacks, overnight stays, weather-related events such as rain, avalanche, summer winds, and so on the hiking trails.

Various types of multi-functional hiking poles exist in the prior art that are related to assisting hikers during hiking. For instance, US20140060598A1 discloses a walking stick chair that includes a main stick, a seat unit, a support unit, and a linking unit. The seat unit includes a sleeve member connected in a fixed position to the main stick, and a seat member connected pivotally to the sleeve member and operable between a folded state and an unfolded state. The support unit is connected pivotally to the main stick. The linking unit is connected pivotally to the support unit and the seat member. When the seat member is at the unfolded state, the walking stick chair serves as a chair, and when the seat member is operated from the unfolded state to the folded state, the walking stick chair is converted from the chair to a walking stick.

U.S. Pat. No. 2,186,456A discloses a traction splint especially adapted for skiers and utilizing a pair of ski sticks as the longitudinal elements of the splint. A more specific aspect of the invention comprises the provision of a ski splint comprising ski sticks for the longitudinal elements and means carried within the sticks for forming the splint in cooperation with said sticks.

The existing solutions related to hiking sticks are ineffective, complex in use, difficult to manufacture, costly, and inefficient. There is a need for an effective and efficient solution that solves the aforementioned problem of assisting injured hikers by providing a new and improved method of constructing a crutch as well as a traction splint by utilizing a pair of hiking poles.

SUMMARY

An object of the present invention is the provision of utilizing a pair of hiking poles to construct medical assistance devices.

An object of the present invention is the provision of a novel, simple, and efficient crutch assembly capable of bearing the partial weight of an injured hiker and enabling the hiker to travel to a nearby location.

An object of the present invention is the provision of a novel, simple, and efficient traction splint, capable of being transported with a particular facility and adapted to be applied effectively and expeditiously to maintain a fractured leg under traction.

While the way that the present disclosure addresses the disadvantages of the prior art will be discussed in greater detail below, in general, the present disclosure provides a method for utilizing a pair of hiking poles comprising the steps of: providing a pair of hiking poles, wherein each hiking pole comprises a first end, an intermediate portion and an oppositely disposed second end; wherein a wrist strap is disposed at the first end; and a tip is disposed at the second end; arranging the pair of hiking poles substantially parallel to each other in an inverted manner such that the tip of each hiking pole lies adjacent to the first end of the remaining hiking pole; passing each hiking pole through the wrist strap of the remaining hiking pole; displacing at least one hiking pole relative to the remaining hiking pole in at least one direction away from the remaining hiking pole such that the first end of each hiking pole substantially lies adjacent to the first end of the remaining hiking pole; thereby enabling formation of knot between the wrist straps of the pair of hiking poles; rotating at least one hiking pole relative to the remaining hiking pole; thereby intertwining the knot of the wrist straps of the pair of hiking poles; interconnecting the second end of the pair of hiking poles by using a fastener for forming a two point of contact tip structure formed by the tips of the pair of hiking poles; and connecting an attachment between the intermediate portion of the pair of hiking poles; thereby constructing a crutch assembly.

In an embodiment, the fastener comprises a cable tie fastener.

In an embodiment, the method for using a pair of hiking poles comprises the additional steps of connecting the attachment between the intermediate portion of the pair of hiking poles by using a pair of fasteners.

In an embodiment, the pair of hiking poles are arranged and interconnected in a substantially V-shaped formation after the construction of the crutch assembly.

In an embodiment, the method for using a pair of hiking poles comprises the additional steps for constructing a traction splint.

Embodiments of the present invention discloses a crutch assembly comprising a pair of hiking poles arranged and interconnected in a substantially V-shaped formation, wherein each hiking pole comprises a first end, an intermediate portion and an oppositely disposed second end; wherein a wrist strap is disposed at the first end; and a tip is disposed at the second end; an intertwined knot configured to provide shoulder support to user, wherein the intertwined knot is formed between the wrist straps of the pair of hiking poles by rotating a hiking pole selected from the pair of hiking poles relative to the remaining hiking pole selected from the pair of hiking poles; a fastener interconnecting the second ends of the pair of hiking poles; a two point of contact tip structure formed by the tips of the pair of hiking poles; and an attachment connected between the intermediate portion of the pair of hiking poles, wherein the attachment is configured to provide a hand grip surface for hiker.

In an embodiment, the fastener comprises a cable tie fastener.

In an embodiment, the attachment is connected between the intermediate portion of the pair of hiking poles by using a pair of fasteners.

In an embodiment, the attachment comprises two tapered holes and two semi-circular cuts.

BRIEF DESCRIPTION OF THE DRAWINGS

A more complete understanding of the present disclosure may be derived by referring to the detailed description and claims when considered in connection with the figures, wherein like reference numerals refer to similar elements throughout the figures.

DETAILED DESCRIPTION

The following description is of exemplary embodiments of the invention only, and is not intended to limit the scope, applicability, or configuration of the invention. Rather, the following description is intended to provide a convenient illustration for implementing various embodiments of the invention. As will become apparent, various changes may be made in the function and arrangement of the elements described in these embodiments without departing from the scope of the invention as set forth herein. It should be appreciated that the description herein may be adapted to be employed with alternatively configured devices having different shapes, components, attachment mechanisms and the like and still fall within the scope of the present invention. Thus, the detailed description herein is presented for purposes of illustration only and not for limitation.

Reference in the specification to "one embodiment" or "an embodiment" is intended to indicate that a particular feature, structure, or characteristic described in connection with the embodiment is included in at least an embodiment of the invention. The appearances of the phrase "in one embodiment" or "an embodiment" in various places in the specification are not necessarily all referring to the same embodiment.

The system as well as the method for utilizing a pair of hiking poles for constructing medical assistance devices will now be described with reference to accompanying drawings, particularly FIGS. 1-22.

Figure 1:
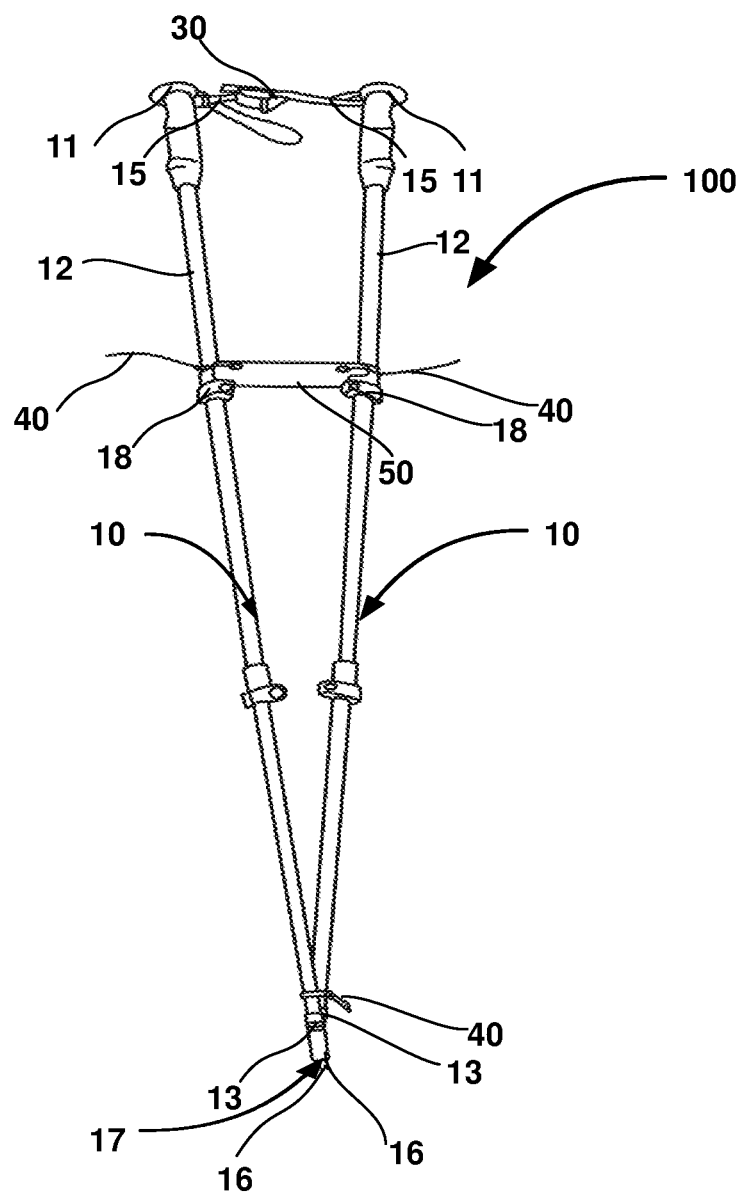
FIG. 1 illustrates a front-perspective view of a crutch assembly, according to an embodiment of the present invention.

Reference is initially made to FIG. 1 which illustrates a front perspective view of a crutch assembly 100, according to an embodiment of the present invention. The crutch assembly 100 comprises a pair of hiking poles 10 arranged and interconnected in a substantially V-shaped formation, a plurality of fasteners 40, and an attachment 50, the entirety of which will be described in greater detail in the below description. The crutch assembly 100 is configured for partial weight bearing and allows a hiker with a mild injury to travel to a trail or a medical help facility.

Both hiking poles 10 are identical in design and method of construction and are individually referred to as "hiking pole 10" for sake of simplicity and ease of understanding. Each hiking pole 10 comprises a first end 11, an intermediate portion 12, and an oppositely disposed second end 13. A wrist strap 15 is disposed of at the first end 11 to prevent unintentional/accidental release of the hiking pole 10 from the hands of the hiker. A tip 16 is disposed at the second end 13 that is configured to provide contact of the hiking pole 10 with the ground. It should be understood that the hiking pole 10 is already known in the art and readily sold by various merchandise using various product names such as but not limited to: Cascade Mountain Tech Aluminum Adjustable Trekking Poles, TrailBuddy Lightweight Trekking Poles, Decathlon hiking pole and so on. Further, the hiking pole 10 comprises a first joint 18, wherein the first joint 18 could translate (move) relative to the intermediate portion 12 along the entire length of the intermediate portion 12.

In various embodiments of the present invention, the plurality of fasteners 40 could include any fastener such as but not limited to: cable tie fastener (zip tie fastener), Velcro fastener, buckle straps, ropes, clips, hook and loop fastener, screws, carabiner, cotter ring, clamps, magnetic couplings, friction couplings, snap-fit couplings, zipper and so on. In an embodiment as seen in FIG. 1, the fastener 40 comprises a cable tie fastener. However, it should be understood that other types of fasteners could be used according to various embodiments of the present invention. The plurality of fasteners 40 of the crutch assembly 100 serves multiple purposes. A fastener 40 is configured for interconnecting the second ends 13 of the pair of hiking poles 10, which will be described in greater detail in the below description. Further, the fastener 40 is configured for connecting an attachment 50 between the intermediate portion 12 of the pair of hiking poles 10, which will be described in greater detail in below description.

Figure 2:
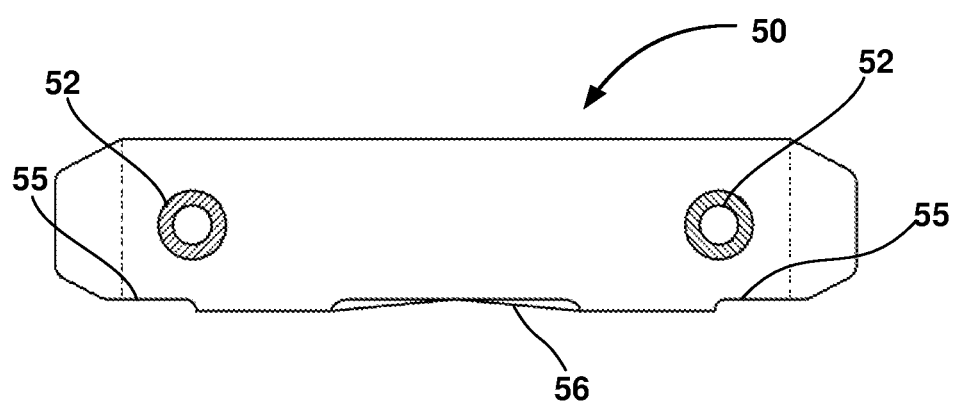
FIG. 2 illustrates a side view of a hand grip of the crutch assembly of FIG. 1, according to an embodiment of the present invention.
Figure 3:
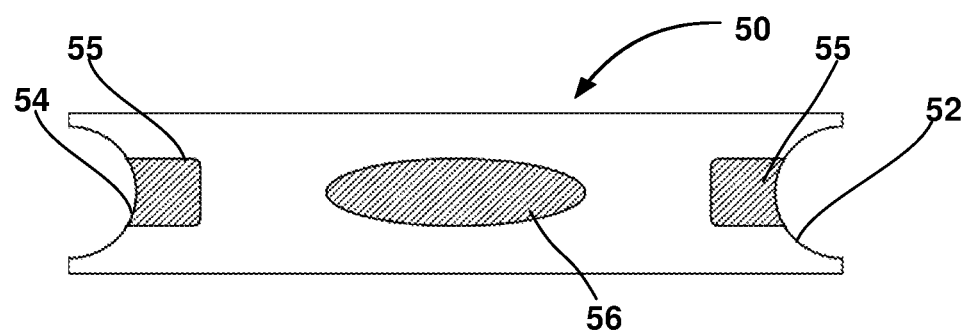
FIG. 3 illustrates a bottom view of a hand grip of the crutch assembly of FIG. 1, according to an embodiment of the present invention.
Figure 21:
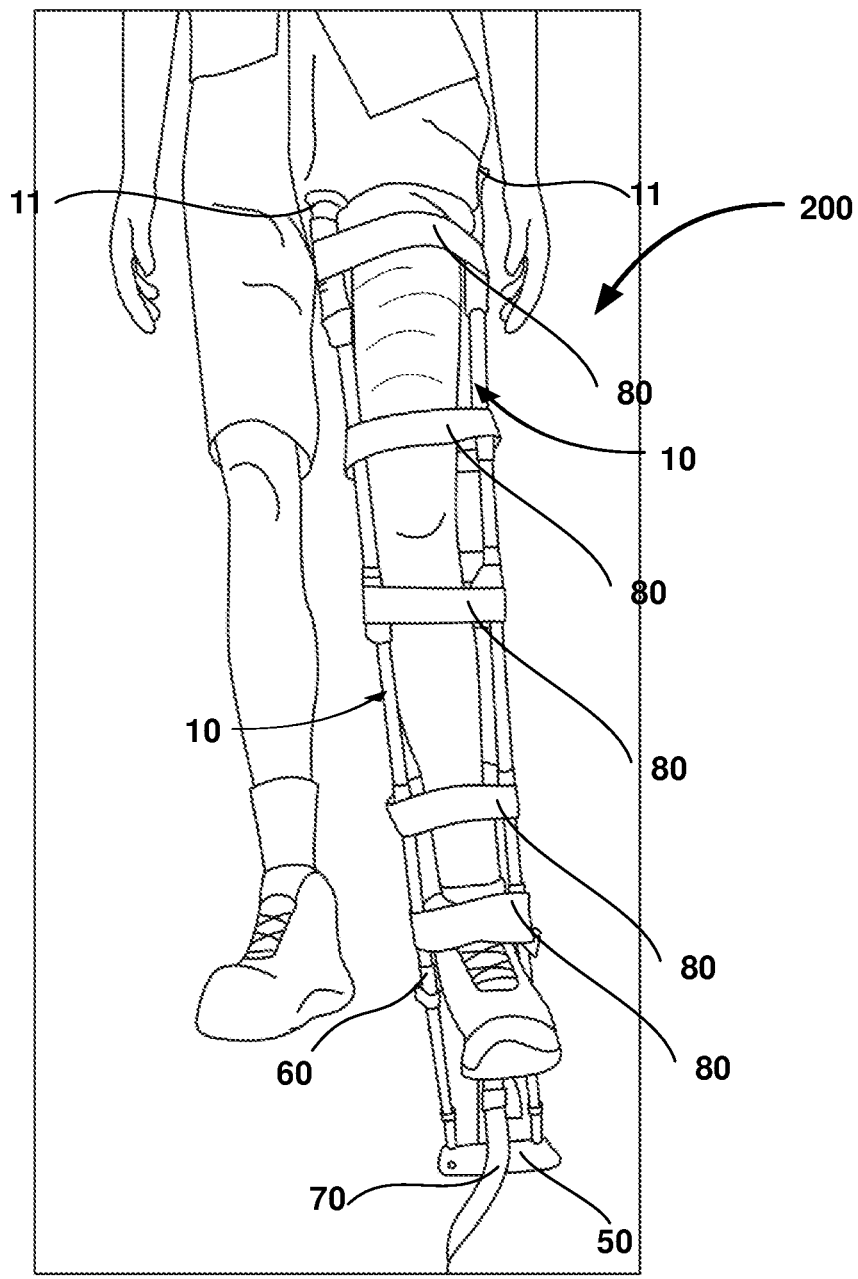
Figure 22:
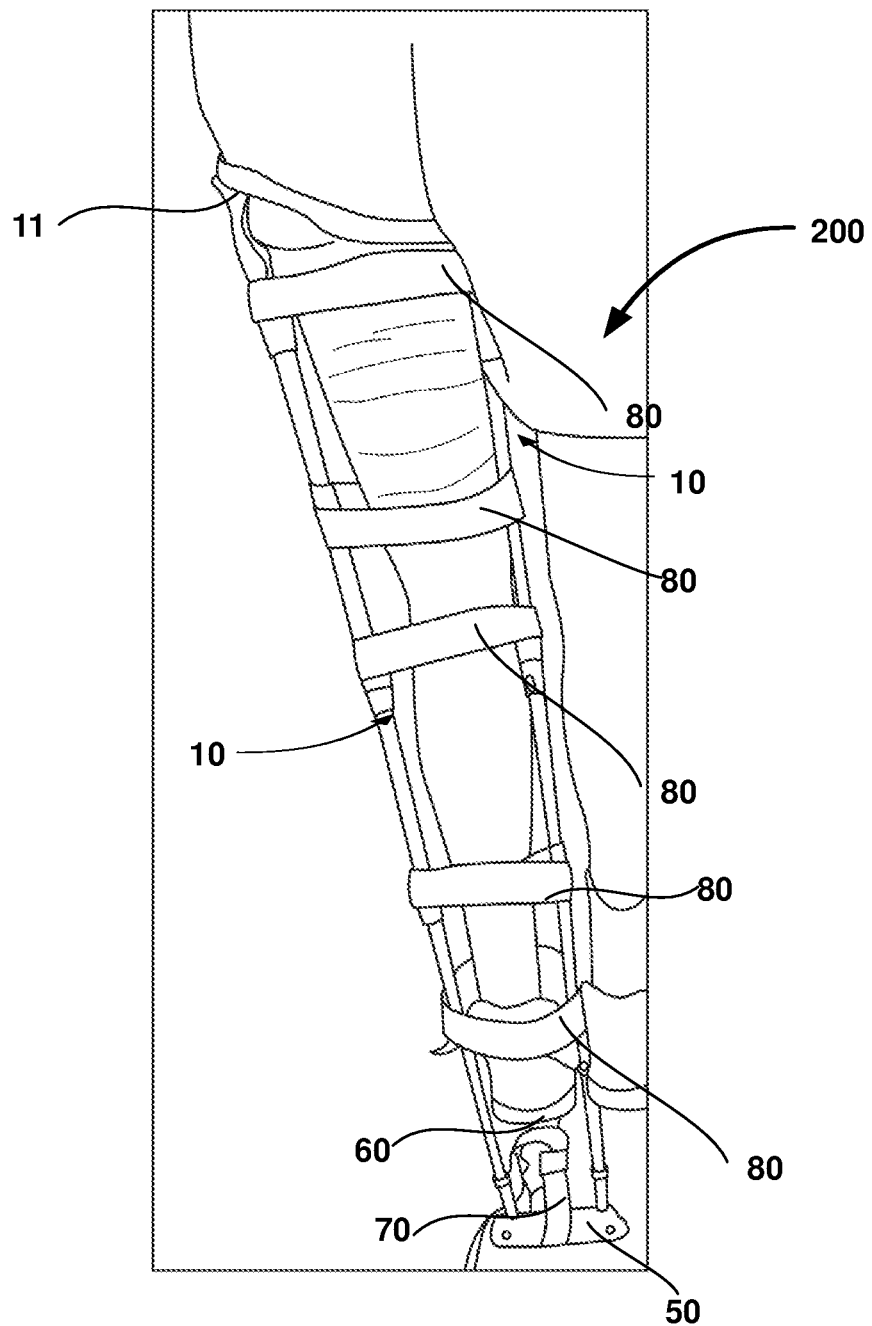

Referring to FIGS. 2-3, a side view and a bottom view of an attachment 50 are depicted respectively, according to an embodiment of the present invention. The attachment 50 is essentially a dowel, that comprises two tapered holes 52 and two semi-circular cuts 54 located on opposite sides of the attachment 50. The attachment 50 serves multiple purposes and is useful in constructing crutch assembly 100 (FIG. 1) as well as traction splint 200 (FIG. 21 and FIG. 22). The two tapered holes 52 are configured for passage of the plurality of fasteners 40, thereby enabling the connection between the intermediate portion 12 of the pair of hiking poles 10 and the attachment 50. Further, the two semi-circular cuts 54 located on opposite sides of the attachment 50 are configured to provide a contact (support) surface against the circular profile (cross-section) of the intermediate portion 12 of the pair of hiking poles 10. Further, a cut-out 55 is disposed of adjacent to each semi-circular cut 54 and the cut-out 55 is disposed on opposite sides of the attachment 50. The cut-out 55 is configured to rest on a first joint 18 of the hiking pole 10. It should be understood that the positioning and number of the tapered holes 52 and semi-circular cuts 54 could be varied depending upon the requirements of the hiker. Further, the two semi-circular cuts 54 could have any other shape part from a semi-circular shape such as but not limited to square, rectangle, triangle, ellipsoid and so on to match the profile (cross-section) of the intermediate portion 12 of the pair of hiking poles 10. Further, in an embodiment as seen in FIGS. 2-3, the attachment 50 comprises a notch 56 that is used to stabilize the buckle strap 70 when the attachment 50 is used for constructing a traction splint 200 (FIGS. 13-22). In an embodiment, the attachment 50 could be made of materials such as but not limited to: wood, plastic, metal, textile, combinations thereof, and so on.

An exemplary method of constructing and using a crutch assembly 100 by utilizing a pair of hiking poles 10 illustrated in FIG. 1 will now be described in reference to FIGS. 4-12.

Figure 4:
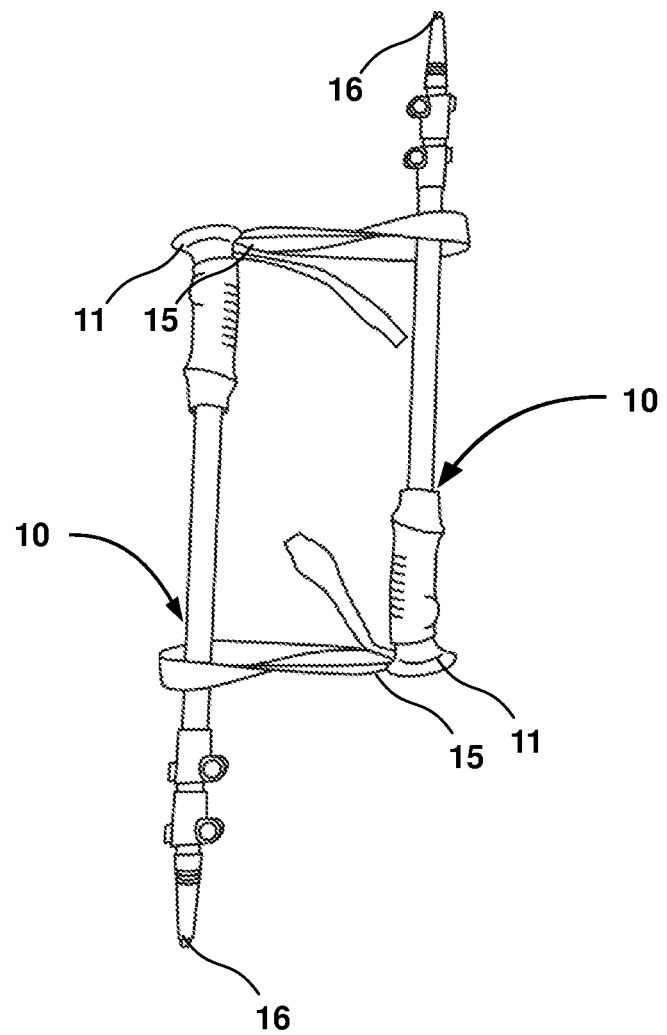
FIGS. 4-10 illustrate various steps performed in a method for constructing a crutch assembly of FIG. 1.

Firstly, a pair of hiking poles 10 are arranged substantially parallel to each other in an inverted manner such that the tip 16 of each hiking pole 10 lies adjacent to the first end 11 of the remaining hiking pole 10. Afterward, as seen in FIG. 4, each hiking pole 10 is passed through a hole formed by straps in the wrist strap 15 of the remaining hiking pole 10.

Figure 5:
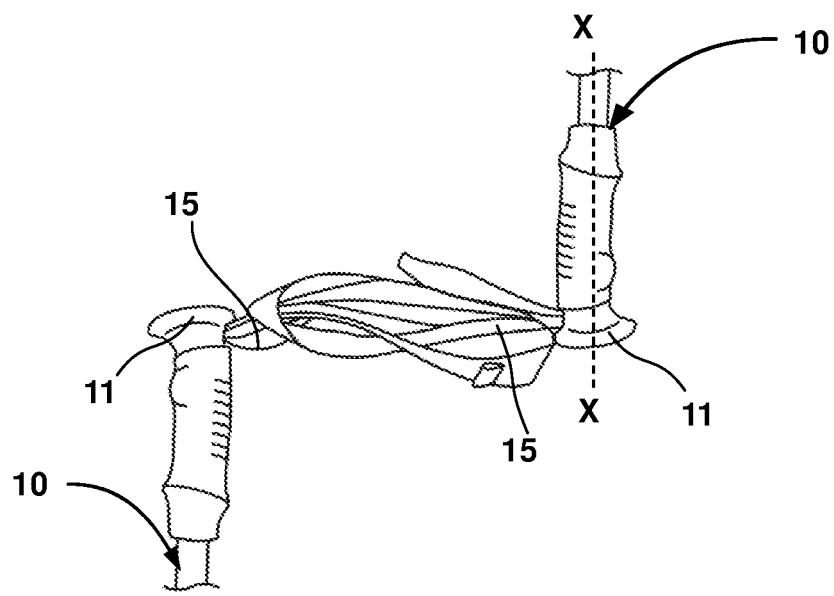
Figure 6:
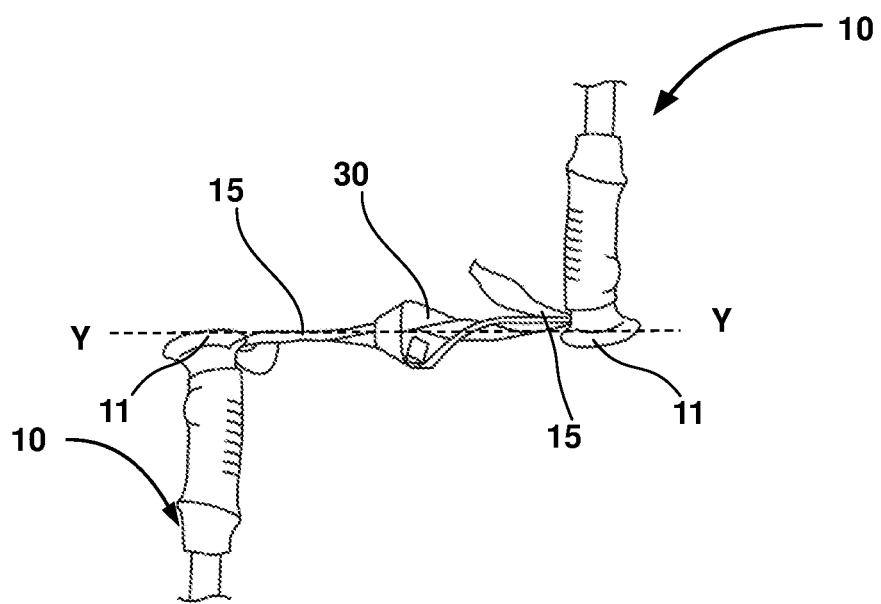

Afterward, as seen in FIG. 5, at least one hiking pole 10 is displaced (translated) relative to the remaining hiking pole 10 in a first direction X-X (shown in dotted lines) away from the remaining hiking pole 10. Afterward, as seen in FIG. 6, at least one hiking pole 10 is displaced (translated) relative to the remaining hiking pole 10 in a second direction Y-Y (shown in dotted lines) away from the remaining hiking pole 10 such that the first end 11 of each hiking pole 10 substantially lies adjacent to the first end 11 of the remaining hiking pole 10, thereby enabling formation of knot 30 between the wrist straps 15 of the pair of hiking poles 10 as seen in FIG. 6.

Figure 7:
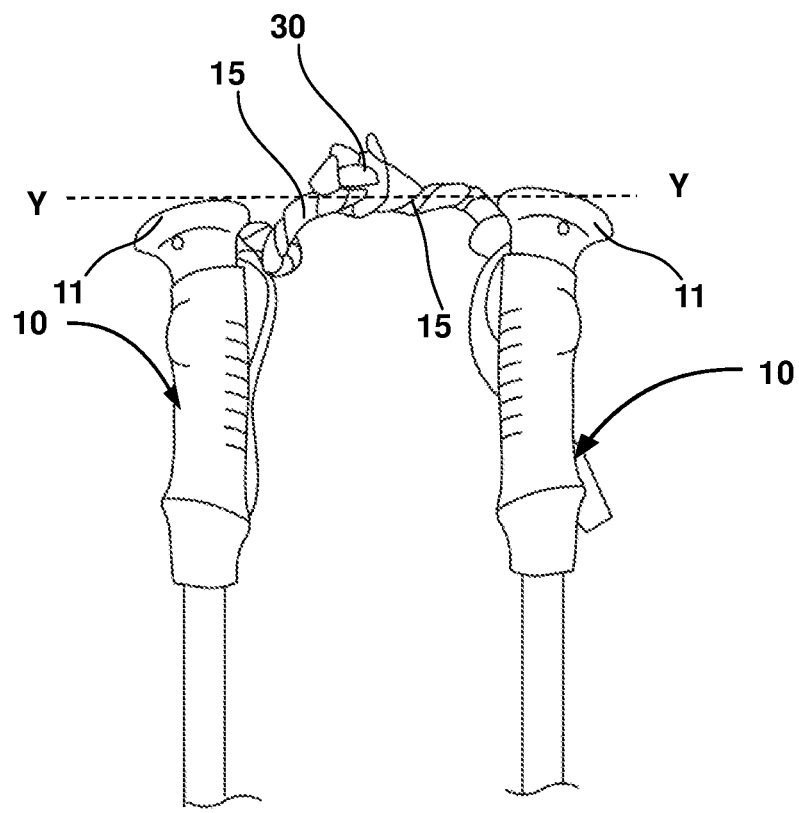

Afterward, the least one hiking pole 10 is rotated relative to the remaining hiking pole 10 along a second direction Y-Y (shown in dotted lines); thereby intertwining the knot 30 of the wrist straps 15 of the pair of hiking poles 10. Further, the intertwining of the knot 30 results in a shorter distance between the pair of hiking poles 10 as seen in FIG. 7. Broadly speaking, the "intertwined knot" 30 is formed between the wrist straps 15 of the pair of hiking poles 10 by rotating a hiking pole 10 relative to the remaining hiking pole 10. The intertwined knot 30 is configured to provide shoulder support to hikers during walking.

Figure 8:
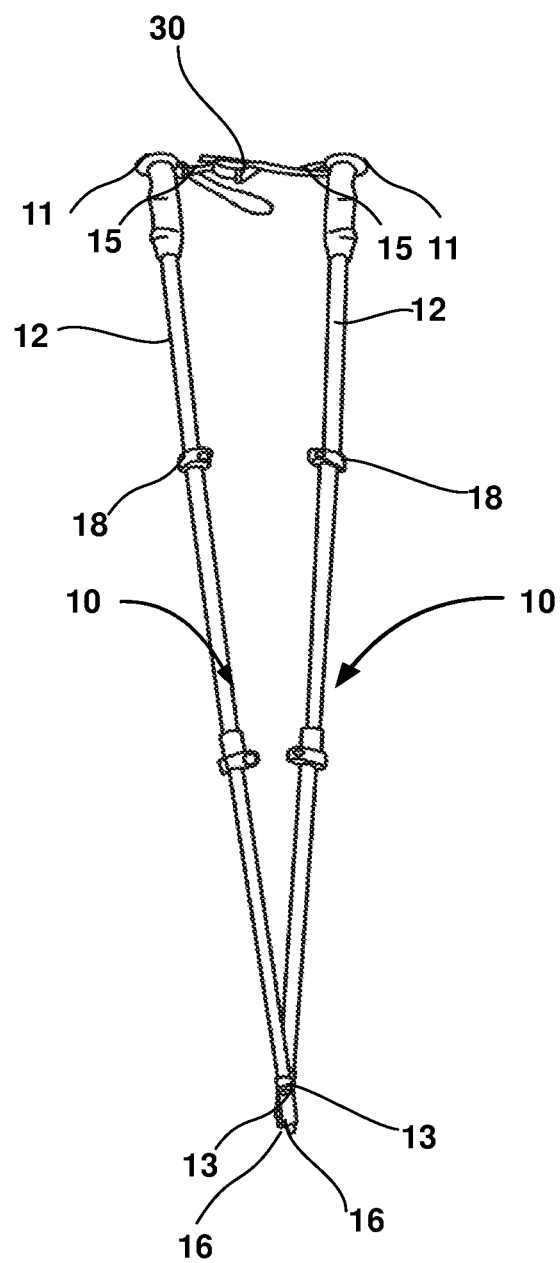
Figure 9:
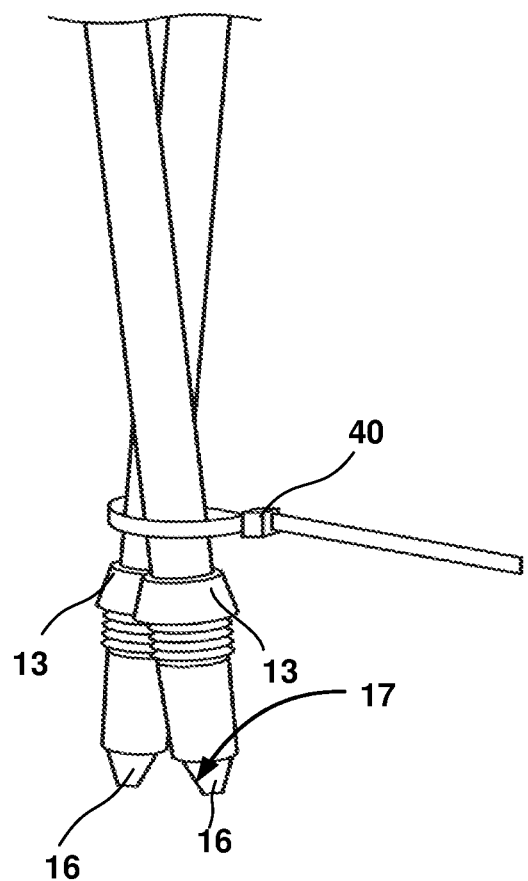

Afterward, the second ends 13 of the pair of hiking poles 10 are interconnected by using a fastener 40 for constructing a two point of contact tip structure 17 formed by the tips 16 of the pair of hiking poles 10 as seen in FIG. 8 and FIG. 9. The two point of contact tip structure 17 has the advantage that the hiker has four points of contact with the ground, that are two tips 16 of the pair of hiking poles 10 and two legs of the hiker, resulting in increased stability and comfort of the hiker during travel.

Figure 10:
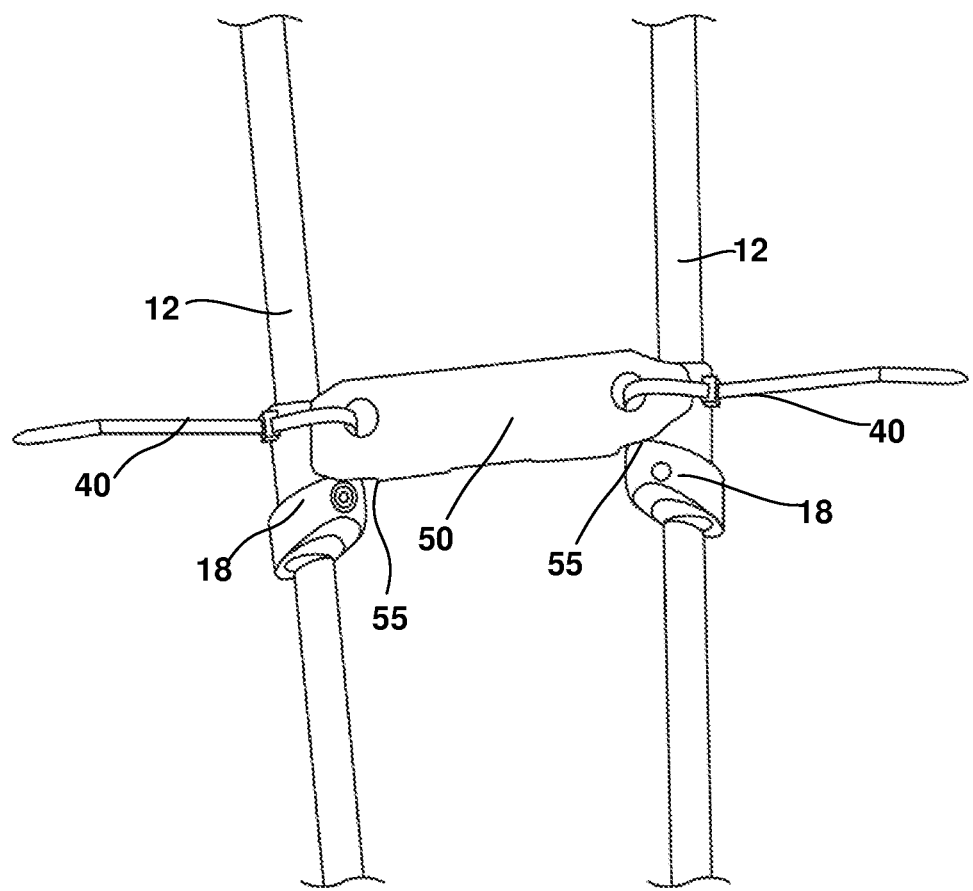
Figure 11:
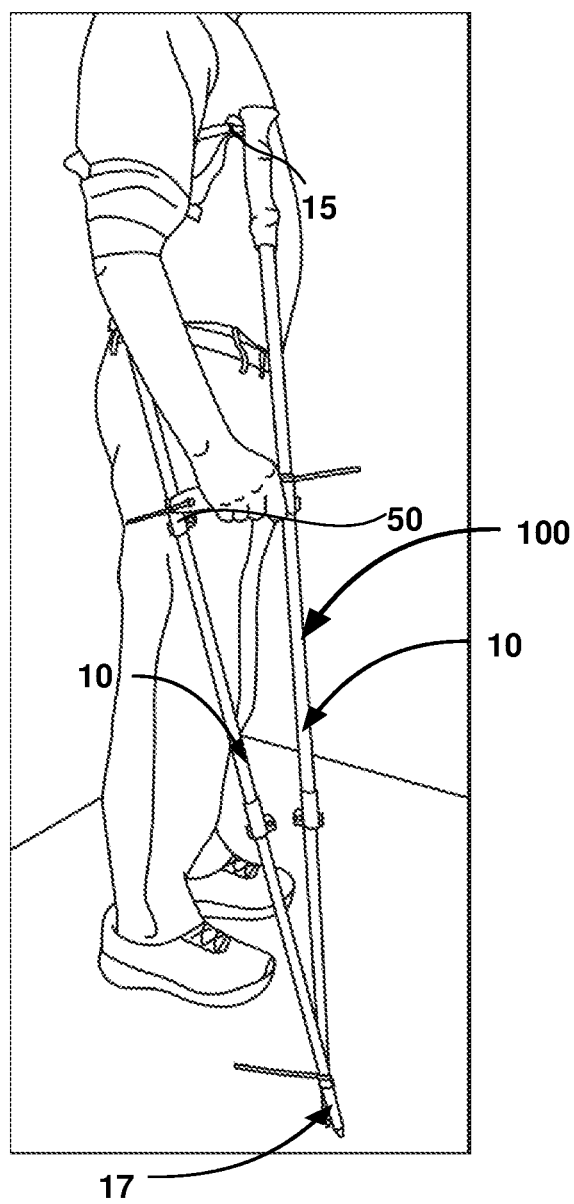
FIG. 11 and FIG. 12 depict a side view and a front view of the crutch assembly of FIG. 1 during use by a hiker respectively.
Figure 12:
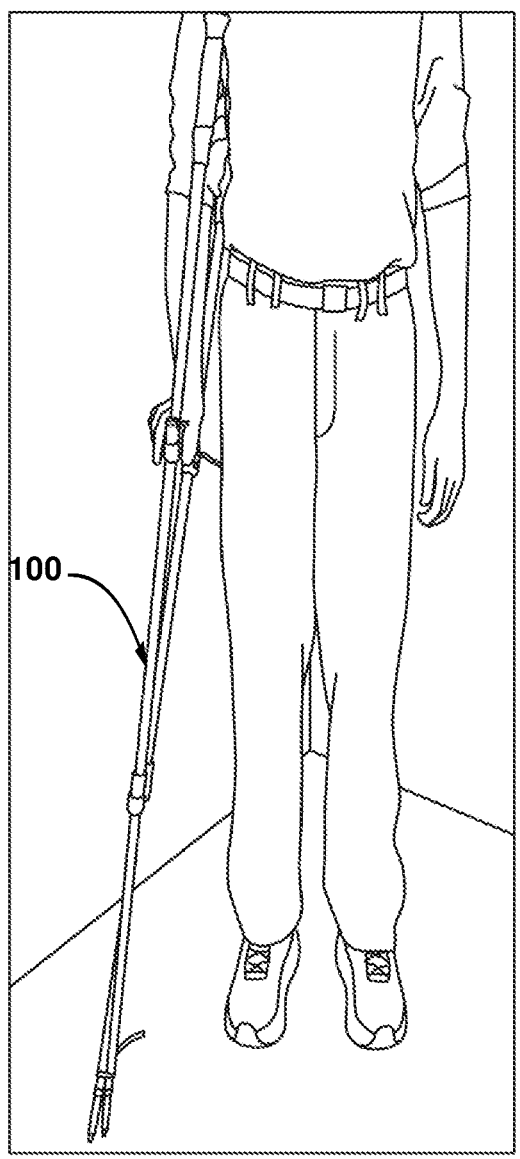

Afterward, as shown in FIG. 10, an attachment 50 is arranged between the intermediate portion 12 of the pair of hiking poles 10. The two semi-circular cuts 54 (FIG. 2 and FIG. 3) of the attachment 50 are aligned with the circular profile (cross-section) of the intermediate portion 12 of the pair of hiking poles 10. Both cut-outs 55 are configured to rest on a first joint 18 of the pair of hiking poles 10. Further, the fasteners 40 connect the two tapered holes 52 of the attachment 50 with the intermediate portion 12 of the pair of hiking poles 10. Thus, the attachment 50 is connected between the intermediate portion 12 of the pair of hiking poles 10, wherein the attachment 50 is configured to provide a hand grip surface for hiker, thereby constructing a crutch assembly 100 as seen in FIG. 1, FIG. 11 and FIG. 12. Further, It should be understood that various steps performed during the construction of the crutch assembly 100 in above mentioned exemplary method could be interchanged. Further, a few steps performed during the construction of the crutch assembly 100 in the above mentioned exemplary method could be skipped for the construction of the crutch assembly 100 with little or no variation.

FIG. 11 and FIG. 12 depict a side view and a front view of the crutch assembly 100 during use by a hiker respectively.

Figure 13:
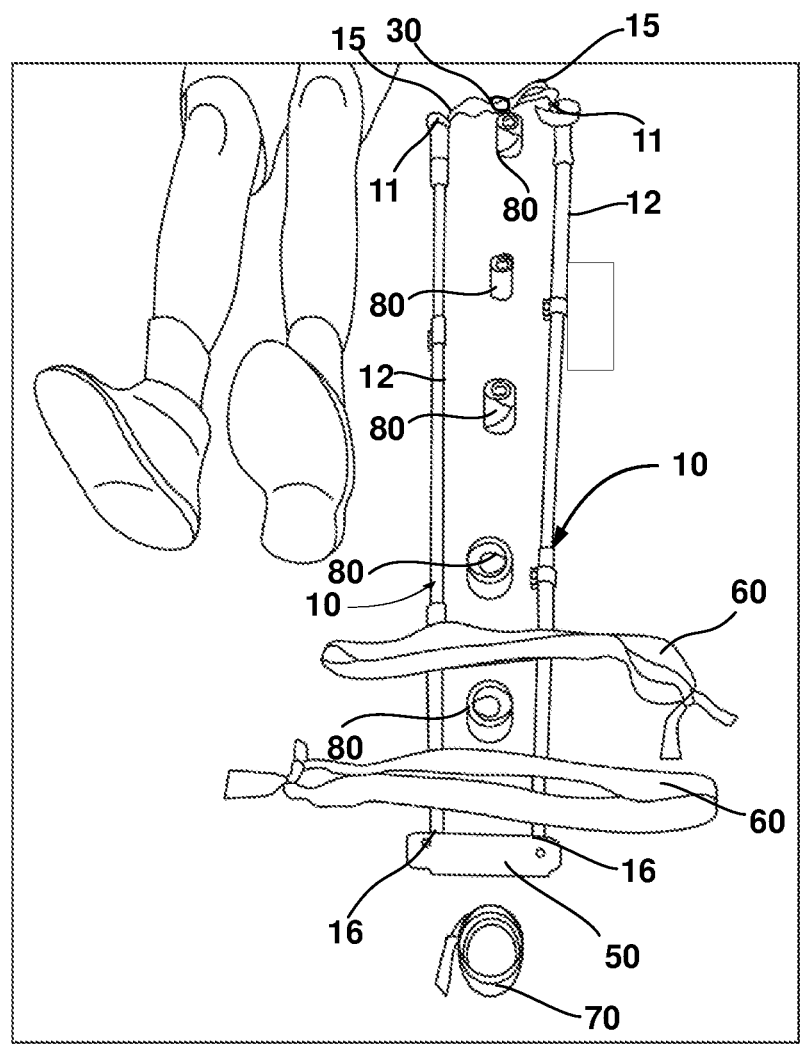
FIG. 13 illustrates a partially assembled front view of the traction splint, according to another embodiment of the present invention.

FIG. 13 illustrates a partially assembled front view of the traction splint 200, according to another embodiment of the present invention. The traction splint 200 comprises a pair of hiking poles 10, an attachment 50, two loop straps 60, a buckle strap 70 and a plurality of Velcro straps 80 (five in number as seen in FIG. 13), the entirety of components could be available (supplied) in the form of a disassembled ready-to-use kit and can be assembled later on to construct the traction splint 200 by using method(s) described in greater detail in below description. The traction splint 200 provides the hiker with an ability to move themselves to an assistance point, and eliminates the risk of serious deterioration due to hazardous environmental conditions and prolonged pain, swelling etc.

An exemplary method of constructing a traction splint 200 by utilizing a pair of hiking poles 10 will now be described in reference to FIGS. 4-6 and FIGS. 14-22.

To construct a traction splint 200, the steps performed in reference to FIGS. 4-6 are repeated with little to no variation. Firstly, a pair of hiking poles 10 are arranged substantially parallel to each other in an inverted manner such that the tip 16 of each hiking pole 10 lies adjacent to the first end 11 of the remaining hiking pole 10. Afterward, as seen in FIG. 4, each hiking pole 10 is passed through a hole formed by straps in the wrist strap 15 of the remaining hiking pole 10.

Afterward, as seen in FIG. 5, at least one hiking pole 10 is displaced (translated) relative to the remaining hiking pole 10 in a first direction X-X (shown in dotted lines) away from the remaining hiking pole 10. Afterward, as seen in FIG. 6, at least one hiking pole 10 is displaced (translated) relative to the remaining hiking pole 10 in a second direction Y-Y (shown in dotted lines) away from the remaining hiking pole 10 such that the first end 11 of each hiking pole 10 substantially lies adjacent to the first end 11 of the remaining hiking pole 10, thereby enabling formation of knot 30 between the wrist straps 15 of the pair of hiking poles 10 as seen in FIG. 6. Thus, the interlocking of wrist straps 15 takes place as a result of the formation of an intertwined knot 30 between the wrist straps 15. Thus, broadly speaking, steps performed in reference to FIGS. 4-6 are repeated with little to no variation in the initial process of constructing a traction splint 200.

In an embodiment as seen in FIG. 13, the hiker is wearing hiking boots during the construction of the traction splint 200. Further, the affected side of the groin of the hiker is padded with a soft material (clothing, gloves, etc.) to protect the soft tissue in the groin and other bony areas.

Figure 14:
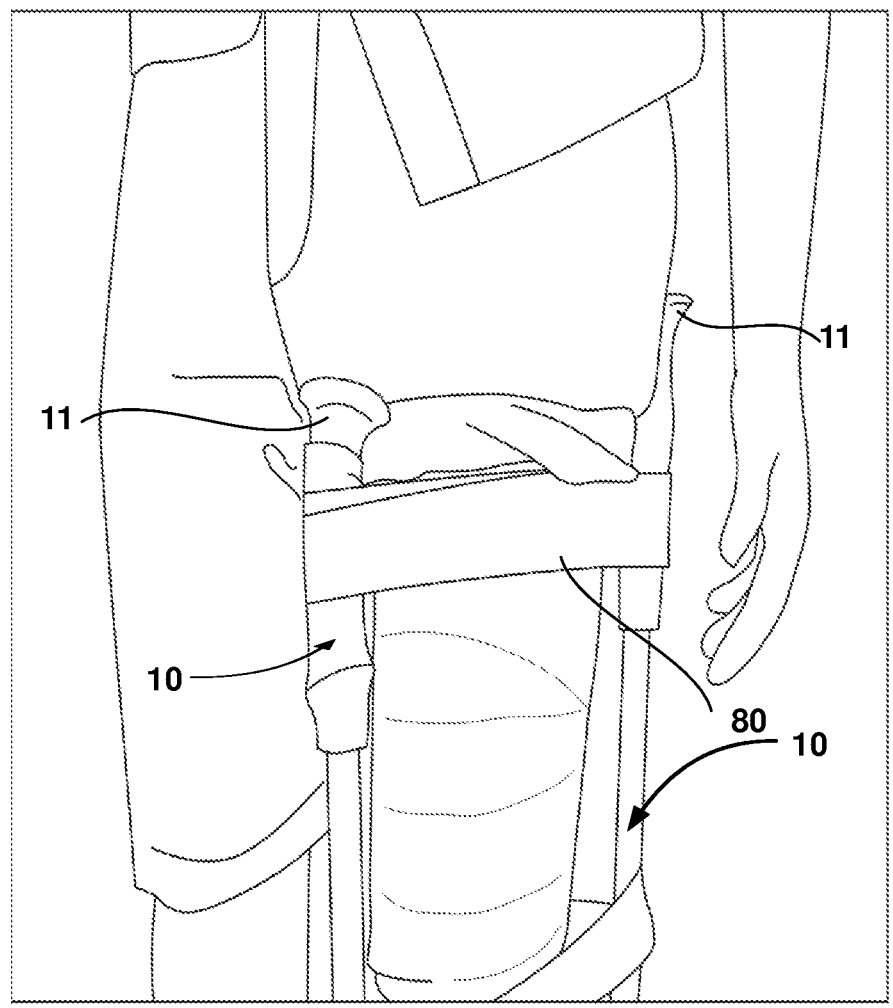
FIGS. 14-22 illustrates various steps performed in a method for constructing a traction splint.

Afterwards, interlocked wrist straps 15 are placed beneath the hip on the side of the injured leg of the hiker. The pair of hiking poles 10 are positioned so that the one Velcro strap 80 is positioned in the groin on the affected side and interlocked wrist straps 15 (not seen in FIG. 14) on the outside (behind) of the injured leg. The first end 11 of a hiking pole 10 between the legs in the groin area will be a few inches shorter than the first end 11 of the remaining hiking pole 10 on the outside of the hip as seen in FIG. 14.

Figure 15:
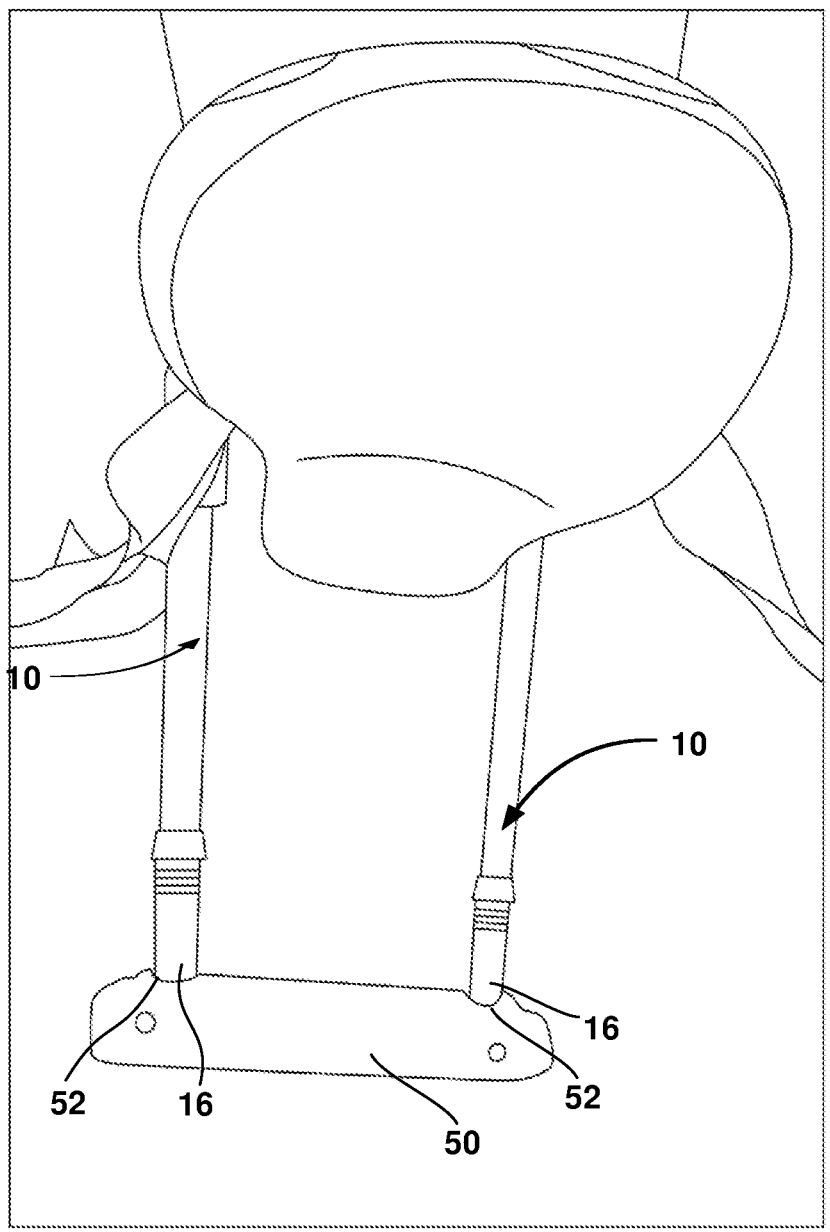

Adjust the lengths of the pair of hiking poles 10 so that the tip 16 of the pair of hiking poles 10 extends beyond the bottom of the foot of the hiker and is equal in length as seen in FIG. 15. Afterwards, the tip 16 of the pair of hiking poles 10 are inserted into the two tapered holes 52 (FIG. 2 and FIG. 3) of the attachment 50 as seen in FIG. 15, wherein the attachment 50 is configured to act as traction point.

Figure 16:
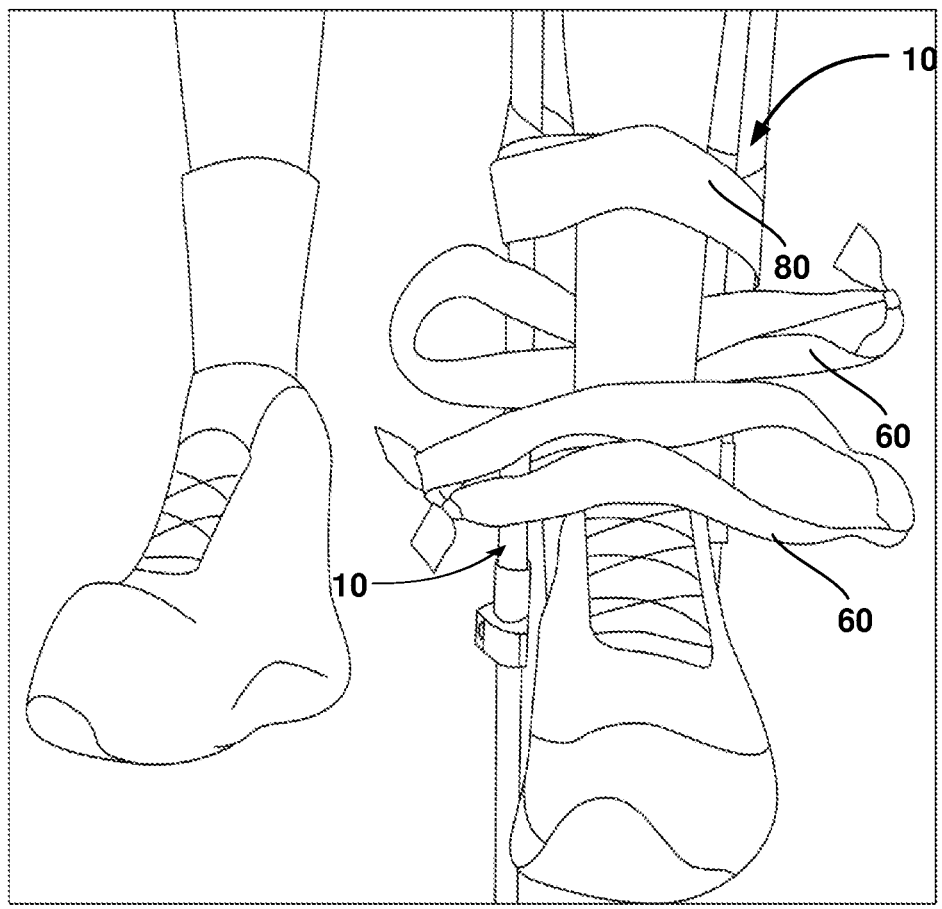
Figure 17:
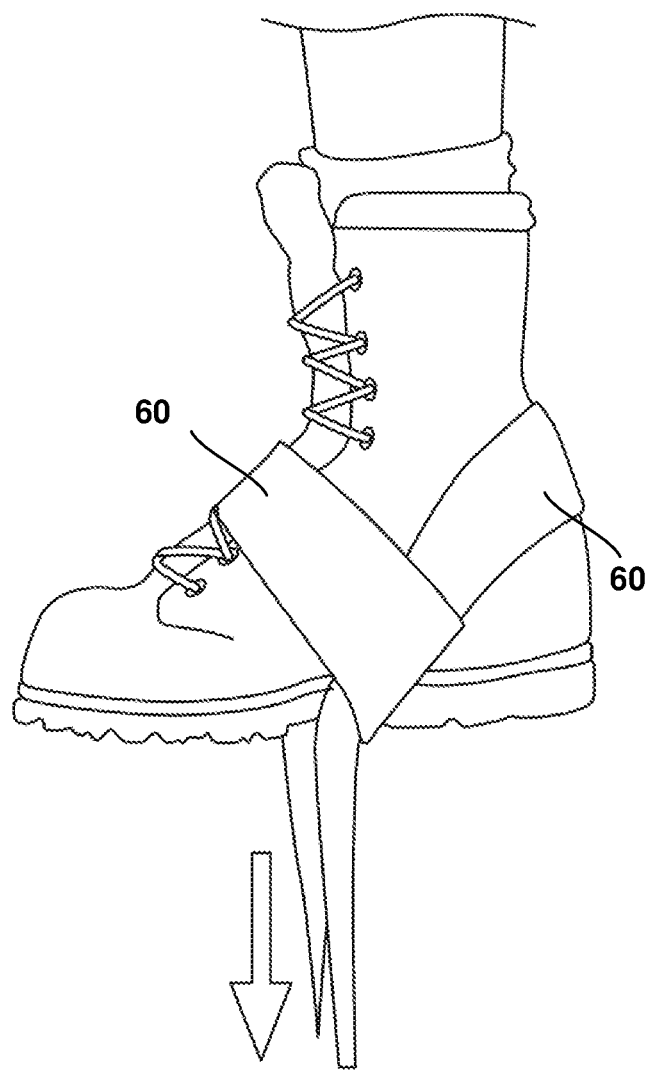
Figure 18:
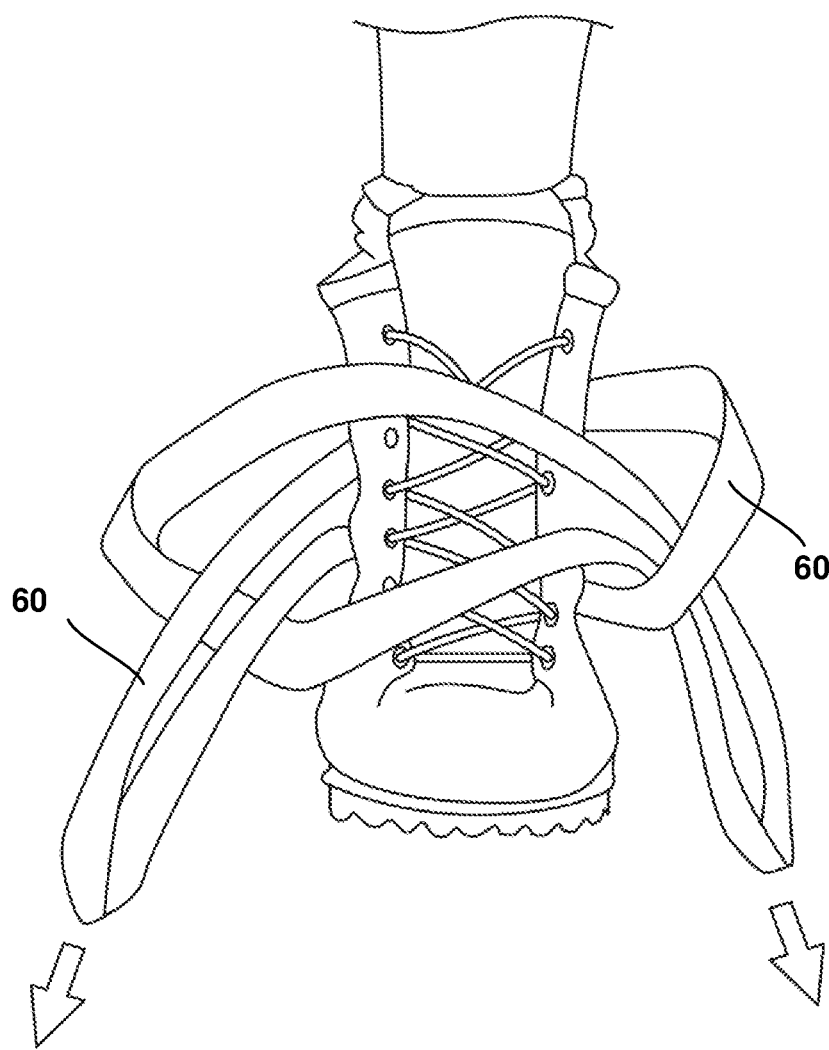

Referring to FIGS. 16-18, afterward, at the ankle of the hiker, place a first knotted loop strap 60 over the pair of hiking poles 10, beneath the ankle, then back over the pair of hiking poles 10 on the inside of the leg. Lay a second knotted loop strap 60 over the top of the pair of hiking poles 10. Now feed the knotted end through the loop that's under the leg. Now feed the knot of the first knotted loop strap 60 from the bottom up through the top of the second knotted loop strap 60. Pull both knots in opposite directions, thereby interlocking the first knotted loop strap 60 and the second knotted loop strap 60 around the ankle. Drape the knotted ends of both first knotted loop strap 60 and the second knotted loop strap 60 under the hiking boot and tie them into a square knot at the arch of the hiking boot so they are snug, but not too tight, against the bottom of the boot. This stirrup will stretch a bit once the traction is applied. Further, position one Velcro strap 80 that surrounds the pair of hiking poles 10 and the leg as seen in FIG. 16.

Figure 19:
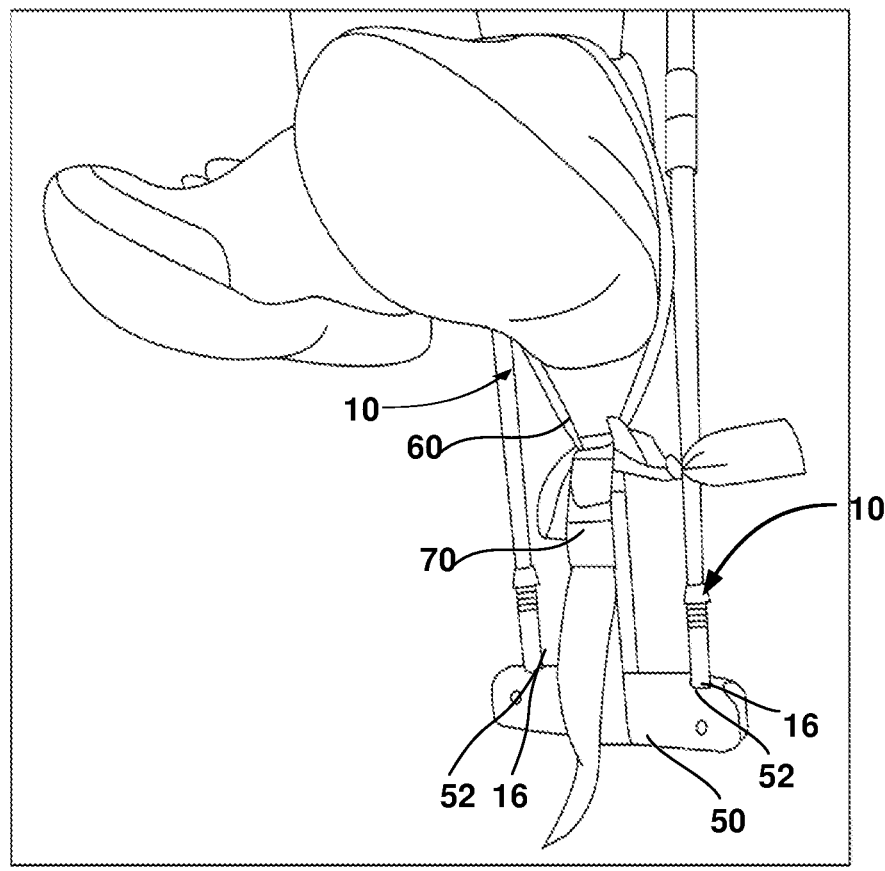

Referring now to FIG. 19, Afterwards, feed a buckle strap 70 between the bottom of the boot and at least one of first loop strap 60 and second loop strap 60. Bring the end of the buckle strap 70 down and around the attachment 50 and back through the buckle of the buckle strap 70.

Figure 20:
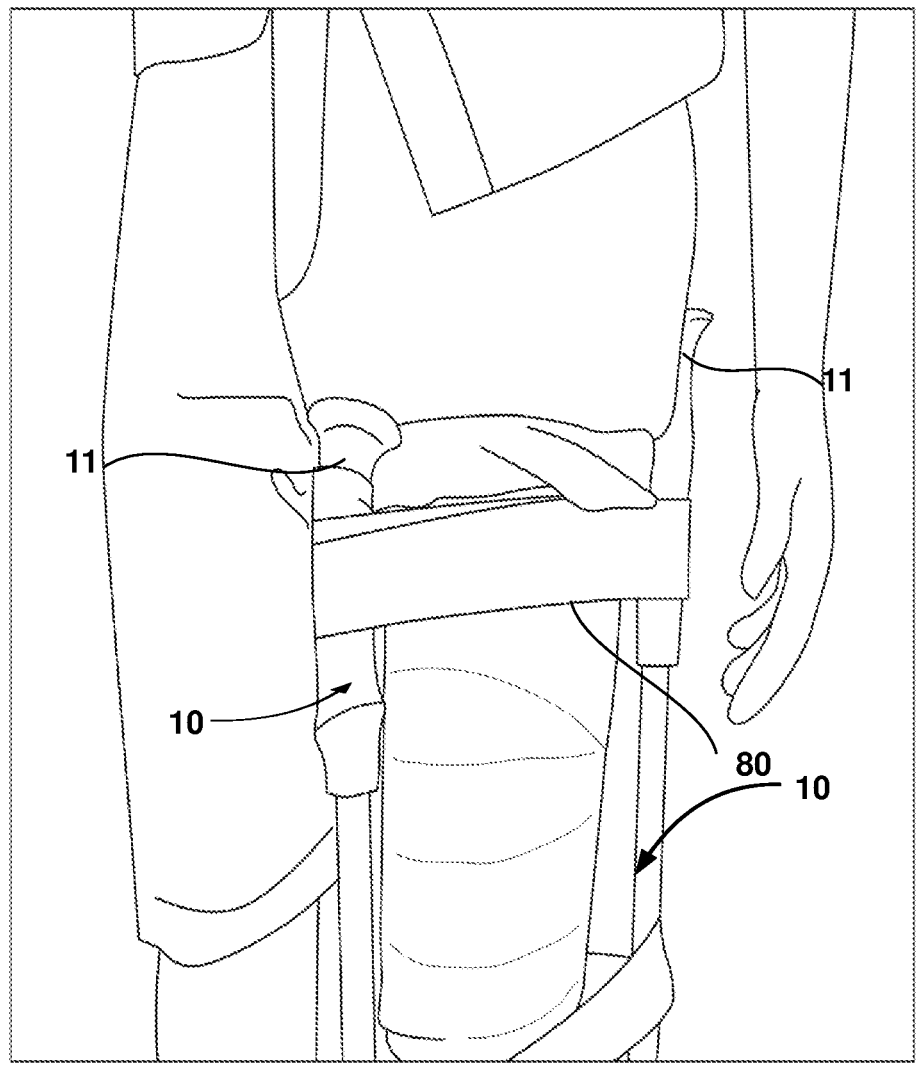

Referring now to FIG. 20, On the upper thigh, secure the pair of hiking poles 10 at the hip using the Velcro straps 80. Begin wrapping from the outside of the thigh, first making one loop around the hiking pole 10, passing beneath the leg, then looping around the hiking pole 10 on the inside of the leg, crossing over the front of the thigh and finally, End by overlapping the Velcro straps 80. Be ready to apply traction on the lower extremity of the hiker gently. Adjust the buckle strap 70 to achieve better positioning. Once pain is relieved and/or the injured lower extremity is approximately equal in length to the uninjured leg, stop adjusting traction. Traction should be maintained until the injured hiker reaches the hospital.

Now the remaining three Velcro straps 80 are secured, that includes one Velcro strap 80 just above the knee of the injured leg, a second Velcro strap 80 just below the tibial plateau of the injured leg, and the third Velcro strap 80 just above the ankle/boot of injured leg as seen in FIG. 21 and FIG. 22.

Afterward, check circulation for the injured hiker that includes pulse, sensation, and movement in the leg and foot on the affected side. If any of these are impaired, repositioning of Velcro straps 80 is required. Afterward, the injured hiker is ready to be transported by using the so-formed traction splint 200 as seen in FIG. 21 and FIG. 22. Further, It should be understood that various steps performed during the construction of the traction splint 200 in above mentioned exemplary method could be interchanged. Further, a few steps performed during the construction of the traction splint 200 in the above mentioned exemplary method could be skipped for the construction of the traction splint 200 with little or no variation.

The various components, and parts of the various embodiments of the crutch assembly 100 as well as traction splint 200 of the present invention are similar and interchangeable. It is obvious to one skilled in the art that the various components, and parts of the crutch assembly 100 of the present invention could be considered for traction splint 200 with little or no variation. Further, it should be understood that the method for utilizing a pair of hiking poles for constructing medical assistance devices could be performed at any location such as but not limited to hiking trails.

Finally, while the present invention has been described above with reference to various exemplary embodiments, many changes, combinations, and modifications may be made to the exemplary embodiments without departing from the scope of the present invention. For example, the various components may be implemented in alternative ways. These alternatives can be suitably selected depending upon the particular application or in consideration of any number of factors associated with the operation of the device. In addition, the techniques described herein may be extended or modified for use with other types of devices. These and other changes or modifications are intended to be included within the scope of the present invention.

What is claimed is:

1. A method for utilizing a pair of hiking poles (10), comprising the steps of:
   providing a pair of hiking poles (10), wherein each hiking pole (10) comprises a first end (11), an intermediate portion (12), and an oppositely disposed second end (13); wherein a wrist strap (15) is disposed at the first end (11); and a tip (16) is disposed at the second end (13);
   arranging the pair of hiking poles (10) substantially parallel to each other in an inverted manner such that the tip (16) of each hiking pole (10) lies adjacent to the first end (11) of the remaining hiking pole (10);
   passing each hiking pole (10) through the wrist strap (15) of the remaining hiking pole (10);
   displacing at least one hiking pole (10) relative to the remaining hiking pole (10) in at least one direction away from the remaining hiking pole (10) such that the first end (11) of each hiking pole (10) substantially lies adjacent to the first end (11) of the remaining hiking pole (10); thereby enabling the formation of a knot (30) between the wrist straps (15) of the pair of hiking poles (10);
   rotating at least one hiking pole (10) relative to the remaining hiking pole (10); thereby intertwining the knot (30) of the wrist straps (15) of the pair of hiking poles (10);
   interconnecting the second end (13) of the pair of hiking poles (10) by using a fastener (40) for forming a two point of contact tip structure (17) formed by the tips (16) of the pair of hiking poles (10); and
   connecting an attachment (50) between the intermediate portion (12) of the pair of hiking poles (10); thereby constructing a crutch assembly (100).

2. The method for using a pair of hiking poles (10) according to claim 1, wherein the fastener (40) comprises a cable tie fastener.

3. The method for using a pair of hiking poles (10) according to claim 1, comprising the additional step of connecting the attachment (50) between the intermediate portion (12) of the pair of hiking poles (10) by using a pair of fasteners (40).

4. The method for using a pair of hiking poles (10) according to claim 1, wherein the pair of hiking poles (10) are arranged and interconnected in a substantially V-shaped formation after construction of crutch assembly (100).

5. The method for using a pair of hiking poles (10) according to claim 1, comprising the additional steps for constructing a traction splint (200).

6. The method for using a pair of hiking poles (10) according to claim 1, wherein the attachment (50) is formed of a material comprising wood, plastic, metal, textile and combinations thereof.

7. A crutch assembly (100) comprising:
- a pair of hiking poles (10) arranged and interconnected in a substantially V-shaped formation, wherein each hiking pole (10) comprises a first end (11), an intermediate portion (12) and an oppositely disposed second end (13); wherein a wrist strap (15) is disposed at the first end (11); and a tip (16) is disposed at the second end (13);
- an intertwined knot (30) configured to provide shoulder support to user, wherein the intertwined knot (30) is formed between the wrist straps (15) of the pair of hiking poles (10) by rotating a hiking pole (10) selected from the pair of hiking poles (10) relative to the remaining hiking pole (10) selected from the pair of hiking poles (10);
- a fastener (40) interconnecting the second ends (13) of the pair of hiking poles (10);
- a two point of contact tip structure (17) formed by the tips (16) of the pair of hiking poles (10); and
- an attachment (50) connected between the intermediate portion (12) of the pair of hiking poles (10), wherein the attachment (50) is configured to provide a hand grip surface for hiker.

8. The crutch assembly (100) according to claim 7, wherein the fastener (40) comprises a cable tie fastener.

9. The crutch assembly (100) according to claim 7, wherein the attachment (50) is connected between the intermediate portion (12) of the pair of hiking poles (10) by using a pair of fasteners (40).

10. The crutch assembly (100) according to claim 7, wherein the attachment (50) comprises two tapered holes (52) and two semi-circular cuts (54).

11. The crutch assembly (100) according to claim 7, wherein the attachment (50) is formed of a material comprising wood, plastic, metal, textile and combinations thereof.

* * * * *